United States Patent [19]
Mattioli

[11] Patent Number: 5,526,073
[45] Date of Patent: Jun. 11, 1996

[54] APPARATUS FOR TOPOGRAPHICAL ANALYSIS OF CORNEA

[75] Inventor: Renzo Mattioli, Rome, Italy

[73] Assignee: Optikon Oftalmologia S.p.A., Italy

[21] Appl. No.: 124,102

[22] Filed: Sep. 20, 1993

[30] Foreign Application Priority Data

Sep. 23, 1992 [IT] Italy ................................. RM92A0688

[51] Int. Cl.$^6$ ........................................................ A61B 3/10
[52] U.S. Cl. ........................... 351/212; 351/205; 351/211
[58] Field of Search ..................................... 351/205, 208, 351/211, 212, 221, 247

[56] References Cited

U.S. PATENT DOCUMENTS

| | | | |
|---|---|---|---|
| 4,569,576 | 2/1986 | Karpov et al. | 351/212 |
| 5,088,203 | 2/1992 | Neiswander | 33/200 |
| 5,106,183 | 4/1992 | Yoder, Jr. | 351/212 |

FOREIGN PATENT DOCUMENTS

| | | |
|---|---|---|
| 2368097 | 5/1978 | France . |
| WO84/04882 | 12/1984 | WIPO . |
| WO89/01756 | 3/1989 | WIPO . |
| WO91/13583 | 9/1991 | WIPO . |

Primary Examiner—William L. Sikes
Assistant Examiner—Hung Xuan Dang
Attorney, Agent, or Firm—Samuels, Gauthier, Stevens and Reppert

[57] ABSTRACT

Subject matter of this invention is an apparatus to enable the tridimensional shape of a partially reflecting anatomical surface of a human body, specifically the cornea, to be spatially located. The apparatus, which is based upon a computer and a TV camera, comprises a body (11) made of a transparent material (PERSPEX®) wherein a conical hole has been drilled. Circular, frusto-conical, alternatively transparent and opaque, retro-illuminated, reference lines are provided in the conical surface of the hole. Furthermore, the apparatus comprises a photoelectrical couple (17, 18) (an emitter: IRED or LED; and a sensor: photodiode or phototransistor) arranged at diametrically opposed points of the external base of the cone, such that when the cone is moved close to the eye to be analyzed, the apex of the eye intercepts the sight line between the emitter and the sensor at a pre-established distance from the cone. The light patterns reflected from the reference sight lines upon the cornea, as detected from the TV camera arranged near the apex of the cone and upon being suitably processed by said computer, enable the shape of the cornea itself as well as the curvature of all points thereof within a relatively large area to be analyzed. (FIG. 1).

10 Claims, 3 Drawing Sheets

APPARATUS FOR TOPOGRAPHICAL ANALYSIS OF CORNEA

BACKGROUND OF THE INVENTION

1. Field of the Invention

This invention generally relates to an apparatus for topographical analysis of anatomical surfaces and, more particularly to such an apparatus enabling the tridimensional shape of partially reflecting anatomical surfaces to be spatially located. The disclosed apparatus can be specifically but not exclusively employed for topographical analysis of the cornea of a human eye.

2. Description of the Prior Art

The measurement of the shape and curvature of the human eye (corneal topography, cheratometry) is a technique which is being strongly developed in coping with the requirements of the recent refractive surgery techniques, as well as in view of the selection or manufacture of custom-fit contact lenses and for diagnosis of certain pathologies (such as keratoconus, traumas or post-surgical complications etc.). The backgrounds of such techniques are rather old. In 1619 Father Christopher Schneider compared to this effect the image of a window reflected upon the eye to the same image reflected upon balls of different diameters.

After studies of Jesse Ramsden (1796) and Helmotz, in 1881 Javal and Schiotz disclosed a cheratometer (or ophtalmometer), use of which is presently still largely widespread, enabling the average corneal curvature to be measured based upon the reflected image of a suitable reference sight line projected upon the eye, according to various meridian axes.

In the meantime, in 1880, Antonio Placido firstly disclosed the use of a disk having concentric white rings upon a black background, presently still known as Placido Disk. The reflected images are observed through a pin-point hole placed at the center of the disk and the shapes of the circles and their mutual distances enable a qualitative, but significant for a skilled person, analysis of the corneal curvature to be made in all areas involved in visual activities.

An alternative approach, mainly employed in surgery operations, provides for a "disposable" cylinder to be placed upon the eye and having alternated black and white cylindrical reference sight lines or so-called "mires" internally formed therein with a height suitably increasing starting from the eye (as taught by Dr. William F. Maloney).

Subsequently, various illuminating systems (as in U.S. Pat. No. 3,248,162, No. 4,772,115 and No. 5,018,850) and a photographic camera to record the measurements (see in U.S. Pat. No. 3,598,478 and No. 3,797,921) have been added to the Placido Disk. The pictures so obtained can also be picked up by a TV camera and processed by a computer (LSU Corneal Topography System and Photocheratoscope Nidek PKS-1000).

A subsequent step provided for arranging the TV camera directly behind the reference sight lines. In a specific variant, the reference sight lines maintain a shape similar to the shape they have in a Placido Disk (retro-illuminated disk or dome). In other variants (such as in U.S. Pat. No. 3,598,478 and No. 4,863,260) the shape of the illuminating device is such that it can protrude into the superciliary arch.

An advantage of this second approach, of course, is that it provides a more compact apparatus which is adapted to project the most external reference sight lines from a significantly larger angle and with less shadows (eyebrow, nose, etc.). The weakness point of this approach, however, is that even the smallest error in the position of the eye when the measurement is carried out causes a noticeable error when the resulting data are analysed. For instance, when the eye is moved closer by 2 mm, an error is caused corresponding to a variation from 43 to 42 diopters, while in topography an accuracy of ¼ diopter is required.

The technique as described in U.S. Pat. No. 4,863,260 (and in U.S. Pat. No. 5,018,850), for instance, uses two intersecting lasers and this makes the measurement operation extremely sensitive and dependent on the user's hand, without even the possibility to know the accuracy with which the measurement has been performed (in view of the fact that the lasers are turned off when the picture is taken).

The broad object of this invention is to provide an apparatus for topographical analysis, particularly for the cornea, wherein all drawbacks of the prior art are eliminated, particularly in so far as the accuracy and repeatability of the measurements, as well as the independence and the oversensitivity of the involved manual operations are concerned.

A particular object, therefore, is to provide an apparatus adapted to pick up and to process the image of an eye only when the eye certainly is in a reference position, thereby assuring a greater than usual accuracy.

SUMMARY OF THE INVENTION

Considered in its whole, the apparatus according to the invention fulfils all economy and construction simplicity requirements, which make it available to a very large number of optics and ophtalmology operators.

Further details and advantages of this invention will be apparent from the following description with reference to the annexed drawings wherein the preferred embodiment of this invention is disclosed by way of illustration and not of limitation.

DESCRIPTION OF THE PREFERRED EMBODIMENT(S)

Figure 1:
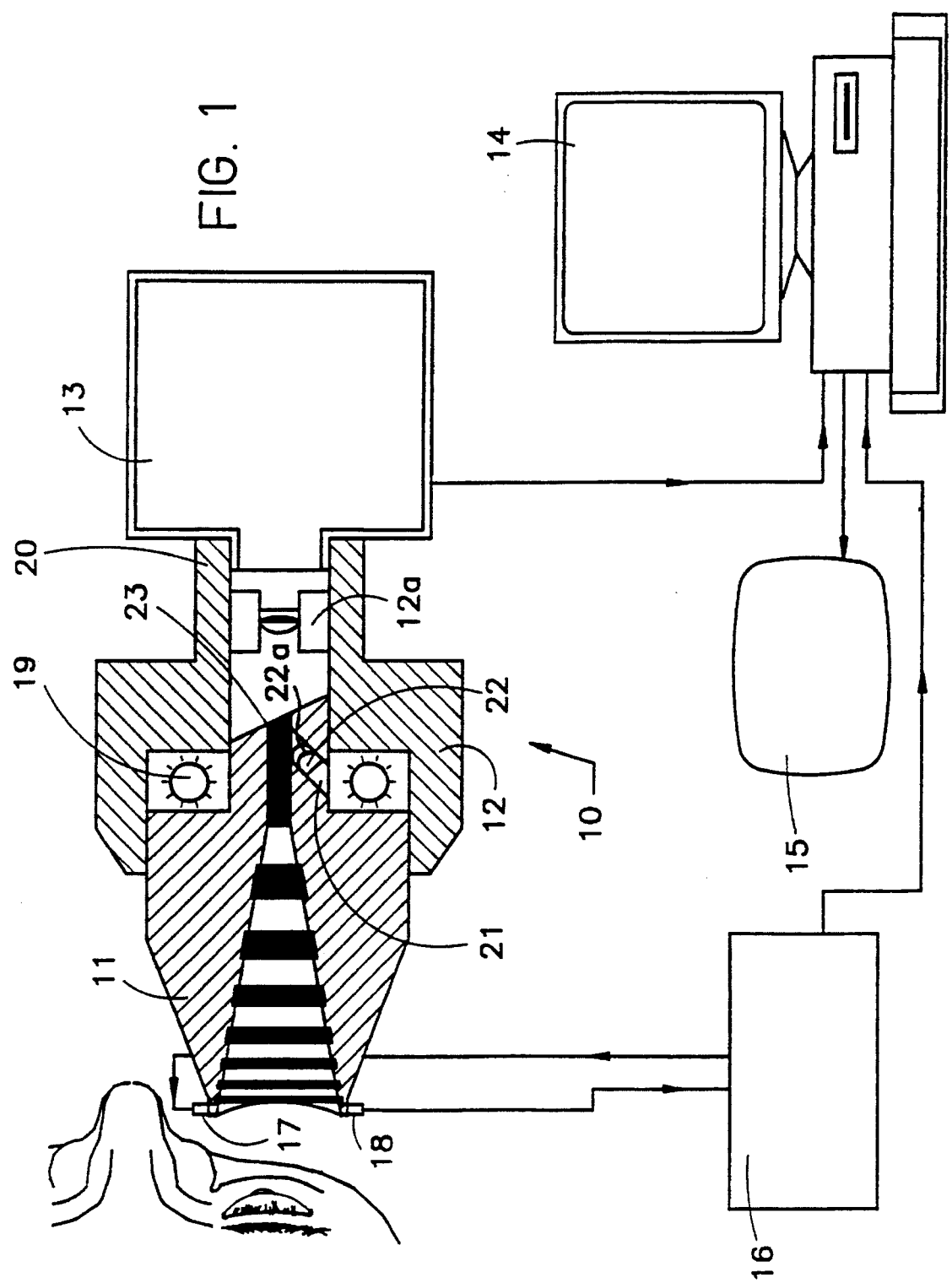
FIG. 1 shows a partially diagrammatic and partially cross-sectional view of the assembly of the apparatus and of its auxiliary systems.
Figure 3:
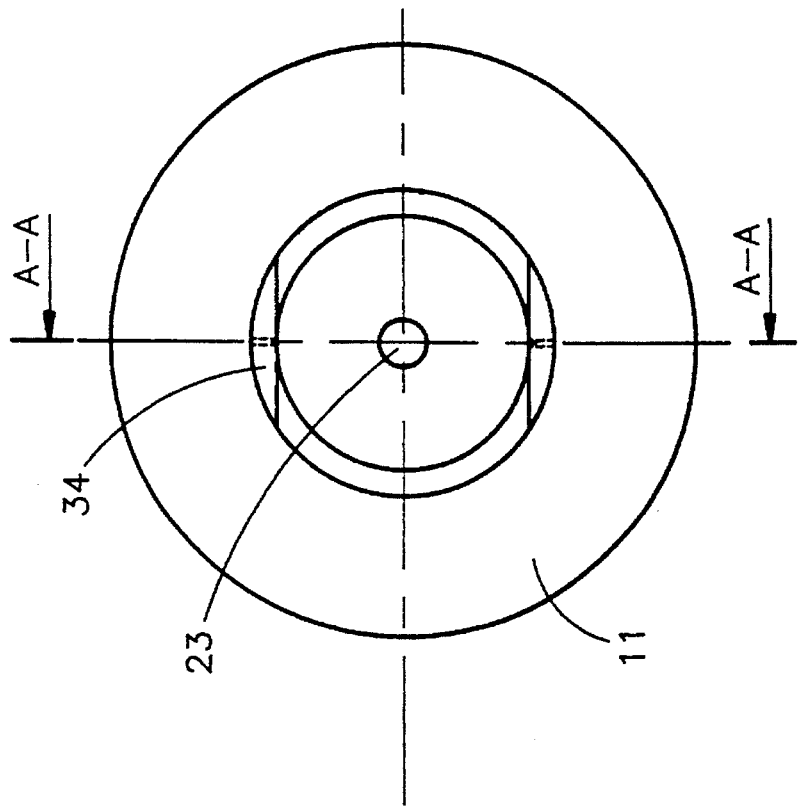
FIG. 3 shows a front end view.
Figure 2:
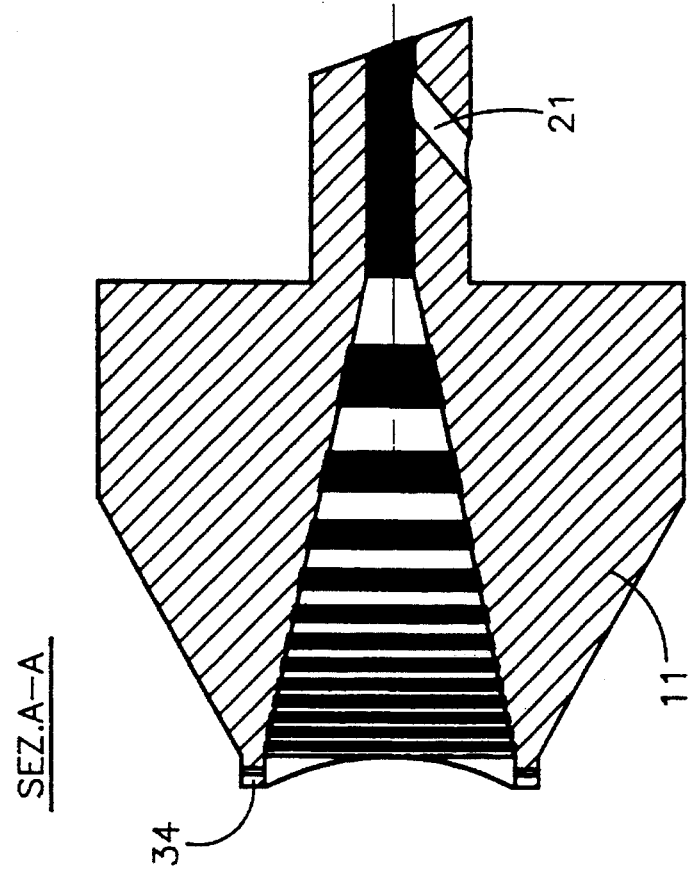
FIG. 2 shows an axial cross-sectional view of the body built in the apparatus for mounting the reference sight lines.

A broad view of the apparatus is shown in FIG. 1. It comprises a head section 10 including a body portion 11, operating as a support member for the reference sight lines or mires, mounted thereupon by means of a suitable adapter member 12 containing the lens 12a and a TV camera 13. The TV camera 13 is operatively connected to a computer 14 equipped with an image picking up (acquisition) section (card) connected to an analogue monitor 15 and interconnected with a corneal apex position detecting device 16 by means of a photoelectric pair 17, 18 arranged on the edge 34 of said body member 11.

As far as the details of said component members are concerned, the body member 11 operating as a support member for said reference sight lines, is made of a transparent material (PERSPEX®) wherein a conical axial through hole is drilled. Frusto-conical, alternatively opaque and transparent sectors are drawn on the internal wall of said cone by means of a painting (coating) or turning operation or by means of point and metal deposition techniques, provided that such an operation is performed with an accuracy of about 1/100 mm.

The geometrical requirements for such frusto-conical circular sectors provide that the alternatively white-black and black-white edges of the reflected images as seen from the TV camera 13 (for instance at a distance of 100 mm from the corneal apex) upon a sphere of 7,85 mm diameter (average apex curvature of a human eye) placed for instance at a distance of 2 mm from the last circular sector have to be concentric and equispaced apart from each other. This feature is designed so as to maintain a qualitative compatibility with the reflected image of a Placido Disk or of a photocheratoscope.

The conical arrangement of the reference sight lines or mires, which can be considered as intermediate between a cylindrical and an ideal spherical arrangement, guarantees that the equidistance between said circular sectors be respected even on spheres having a reasonably different diameter.

Two pin-point holes are provided at the base of the cone, in diametrically opposed positions, for enabling a photoelectric pair to be mounted thereat. This photoelectric pair is preferably arranged on a horizontal line perpendicular to the axis of the cone, so that it cannot be significantly intercepted by the eye-brows or by the eyelids, when the device is moved closer to the eye, either the right or the left one, indifferently.

The above mentioned photoelectric pair comprises a photoemitter 17, consisting of a light emitter diode (LED) or of a infra red emitter diode (IRED) or of a lamp or an optical fiber, and a photoreceiver 18, consisting for instance of a photodiode or of a phototransistor. An IRED diode has been shown only by way of illustration in FIG. 4, in view of the fact that such emitter diodes are available also with diameters less than 1 mm, even when the lens is included, and emit at a not-visible frequency, easily filterable by the TV camera, and in view of the fact that such diodes can be turned off during the photographical take.

Furthermore, photodiodes and phototransistors exist having the same dimensions and the same shape of the IRED diodes. The selection between photodiodes and phototransistors is mainly determined by sensitivity and velocity considerations. It is to be understood, therefore, that, even if the specification is drafted in terms of a photodiode or of an IRED, this should in no way be construed in limitative sense.

From an operation view point and by referring to FIG. 1, it should be appreciated that the light beam emitted by IRED diode 17 and received by photodiode 18 has transversal dimensions different from zero and it is intercepted by the eye in measurement position.

The alternated circular sector pattern is retro-illuminated by light sources 19 by utilising the transparency feature of body 11.

Furthermore, an oblique hole 21 opening into axial hole 23 is provided in the axial shank 20 of said body 11 and a light emitting diode 22 cooperating with a semi-transparent mirror or with a prism 22a is housed in said hole 21 in order to provide a reference sight point to be looked at by the patient.

By referring now to FIG. 4, an electronic circuit will be described for detecting the position of the corneal apex at the center of the path between IRED diode 17 and photodiode 18.

IRED diode is periodically turned on by a pulse generator 35 with a suitable on/off ratio (duty cycle), for instance 1/10, at high frequency.

The output of photodiode or phototransistor 18 is connected to two electronic switches 24, 25, which are driven by a pulse generator 35, the first one (24) being driven directly and the other one (25) through an inverter 26. In this way, the above said electronic switches 24, 25 are alternatively and mutually exclusively conductive. The outputs of said two electronic switches are coupled through two sample-and-hold circuits 27a, 27b to the two, inverting and not-inverting, respectively, inputs of a differential amplifier 28. In this way, the differential amplifier 28 measures the differential between the signal as received by photodiode 18 in presence of an emission from IRED diode 17 and the signal as received by photodiode 18 in absence of an emission from IRED diode 17. As a matter of facts, this means that any component due to background noise is excluded from the output signal.

A low-pass filter 29 is connected to the output of differential amplifier 28 and this filter, in turn, is also connected to the inverting inputs of four comparator circuits 30, 31, 32, 33, the not-inverting inputs of which are connected to the interconnection points of a ladder assembly of cascade resistors RV1, R2, R3, R4, RV5, among which resistors RV1 and RV5 may be variable.

Figure 4:
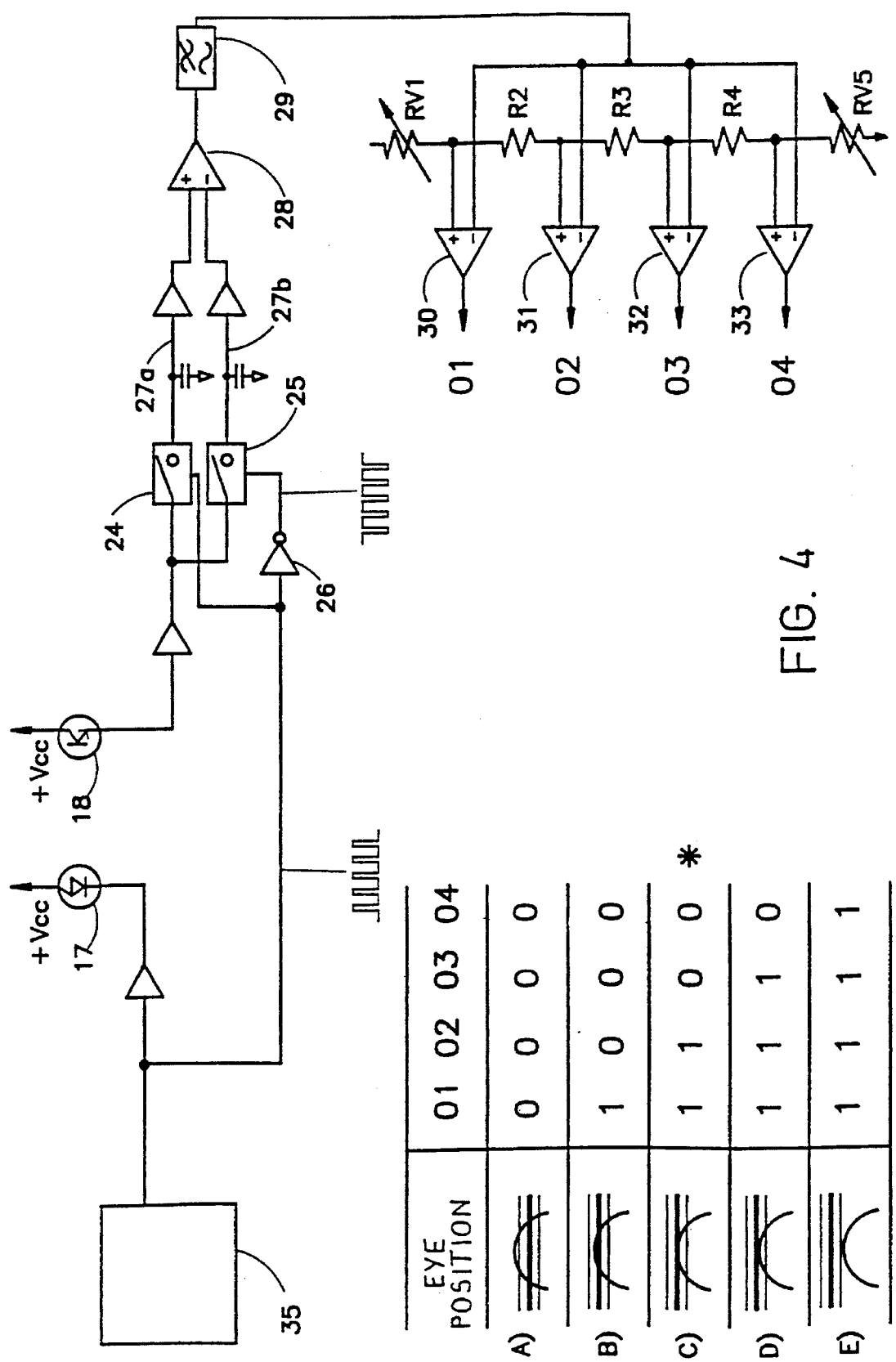
FIG. 4 shows a block diagram of the electronic section for detecting the corneal apex.

It can be appreciated from the True Table annexed to FIG. 4 that, according to the outputs of the above said four comparator circuits 30, 31, 32, 33, it is possible to define five positions for the corneal apex and that, by suitably selecting the five resistors RV1, R2,R3, R4, RV5, a so much accurate position of the eye can be achieved as desired (generically an accuracy of ±0,1 mm) and it is possible to confirm the operation and, therefore, to enable the take only if the corneal apex is placed in the pre-established range. Specifically, it can be observed that in case A the corneal apex is located beyond the utility range; in case B, the corneal apex is located within the utility range but beyond its central point; in case C, the corneal apex is placed exactly on the central point of the utility range; in case D, the corneal apex is located within the utility range but before the central point thereof and, in case E, the corneal apex has not yet entered into the utility range.

I claim:

1. An apparatus for topographical analysis of of a cornea, comprising a TV camera (13) operatively connected to a computer (14) including an analogue monitor and an electronic card having an image take-up circuit, characterized in that said apparatus further comprises a head section (10) containing a body (11) acting as a support member for mires which is mounted by means of a suitable adapter member (12) including the lens (12a) of said TV camera (13), wherein said body (11) is a transparent retro-illuminated body having an axial hole (23) within which alternatively white and black mires are drawn and provided with a photoelectrical pair (17, 18), on the outer edge (34) of said axial hole (23), toward the object to be analyzed, in such a position that said photoelectrical pair transversally intercepts, the apex of the surface of the object to be analyzed when it is at the operation distance, as well as an electrical circuit inserted between said photoelectrical pair (17, 18) and said computer (14), which responds to the surface of the object to be analyzed being properly positioned with respect to said photoelectrical pair (17, 18) so as to warn the operator and/or automatically enable a take-up of the images of said mires upon refection thereof, only when said surface of the object to be analyzed is at a desired distance.

2. The apparatus according to claim 1, characterized in that an internal axial hole (23) provided in said transparent body (11) and having said mires therein is conical.

3. The apparatus according to claims 1 or 2, characterized in that the mires provided on said axial hole of said transparent body comprise circular, alternatively transparent and opaque (white and black) sectors, formed by means of painting or turning operations, or by means of paint or metal deposition techniques.

4. The apparatus according to claim 3, characterized in that said circular sectors fulfil geometrical requirements according to which the alternatively white-black and black-white transitions of the reflected images as they are seen by said TV camera (13) upon a sphere having a diameter corresponding to the normal curvature of the surface to be analysed are concentric and equidistant with respect to one another.

5. The apparatus according to claim 2, characterized in that said transparent body (11) comprises a cylindrical base stem (20) having an oblique radial pin-point hole (21) which intersects with said axial hole (23), and wherein a light emitting diode (22) cooperates with a semi-transparent mirror or a prism, each housed in said oblique radial pin-point hole (21) to provide a reference point to be looked at by the patient.

6. The apparatus according to claim 2, characterized in that said internal axial hole is a frustrum.

7. The apparatus according to claim 1, characterized in that said photoelectrical pair (17, 18) comprises a photoemitter (17) and a photoreceiver (18) mounted in two diametrically opposed seats provided in the edge (34) of a conical hole of said transparent body (11).

8. The apparatus according to claim 7, characterized in that said photoemitter (17) is selected among a light emitting diode (LED), an infra-red emitting diode (IRED), a lamp, and an optical fiber.

9. The apparatus according to claim 7, characterized in that said photoreceiver (18) is selected among a photodiode and a phototransistor.

10. The apparatus according to any one of claims 7 to 9, characterized in that said electronic circuit designed to detect the apex of the surface to be analysed comprises a pulse generator (35), the output of which drives said photoemitter (17) as well as two electronic switches (24, 25), a first (24) of which receives the output of said photoreceiver (18) and is directly driven by said pulse generator (35) and the second (25) of which also receives the output of said photoreceiver (18) and is also driven by said pulse generator (35) by means of an inverter circuit (26), so that said electronic switches are alternatively closed in mutually exclusive sequence; two sample-and-hold circuits (27a, 27b) the inputs of which are connected to the outputs of said electronic switches and the outputs of which are connected to the inputs of a differential amplifier (28); the output of said. differential amplifier being connected through a low-pass filter (29) to the inverting inputs of a set of comparator circuits (30, 31, 32, 33) having their not-inverting inputs variably biased by means of ladder connected, fixed or variable resistors (RV1, R2, R3, R4, RV5).

\* \* \* \* \*